United States Patent
Chen et al.

(10) Patent No.: US 6,728,394 B1
(45) Date of Patent: Apr. 27, 2004

(54) DYNAMIC MEASUREMENT OF OBJECT PARAMETERS

(75) Inventors: Jian-Feng Chen, Issaquah, WA (US); Jin Kim, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 09/504,501

(22) Filed: Feb. 14, 2000

(51) Int. Cl.$^7$ ................................................. G06K 9/00
(52) U.S. Cl. ........................ 382/107; 382/131; 382/278; 382/103; 348/169; 128/915
(58) Field of Search ................................. 382/103, 107, 382/236, 128, 130, 131, 132, 278; 348/402.1, 407.1, 413.1, 414.1, 416.1, 417.1, 169; 128/915, 916

(56) References Cited

U.S. PATENT DOCUMENTS

| | | | | |
|---|---|---|---|---|
| 5,280,530 A | * | 1/1994 | Trew et al. | 382/103 |
| 5,777,690 A | * | 7/1998 | Takeda et al. | 348/699 |
| 5,982,909 A | * | 11/1999 | Erdem et al. | 382/103 |
| 6,012,458 A | * | 1/2000 | Mo et al. | 600/437 |
| 6,192,156 B1 | * | 2/2001 | Moorby | 382/236 |
| 6,201,900 B1 | * | 3/2001 | Hossack et al. | 382/294 |
| 6,295,367 B1 | * | 9/2001 | Crabtree et al. | 382/103 |

OTHER PUBLICATIONS

"Deformable Templates for Tracking and Analysis of Intravascular Ultrasound Sequences" by Fransisco Escolano, First International Workshop of Energy Minimization Methods in Computer Vision and Pattern Recognition, 1997.*

"A Novel Method for Angle Independent Ultrasonic Imaging of Blood Flow and Tissue Motion" by Bohs et al. Biomedical Engineering, IEEE Transactions on , vol.: 38 Issue: 3 , Mar. 1991 Page(s): 280–286.*

\* cited by examiner

*Primary Examiner*—Jon Chang
*Assistant Examiner*—Charles Kim (57) ABSTRACT

Method of dynamically measuring movement of objects is disclosed which uses image processing. In a first step a sequence of images is received and stored. Then, at least a first and second reference point within a first image is determined and identification areas around those reference points are defined. Within a sequential image a search area around the predefined reference points which best match the identification area is searched to determine the displacement of the reference point.

9 Claims, 7 Drawing Sheets

DYNAMIC MEASUREMENT OF OBJECT PARAMETERS

BACKGROUND OF THE INVENTION

The present invention relates to a technique for accurately tracking the movements of objects, in particular of organs, such as heart wall/vessel wall. In clinical examinations it is often necessary to determine the movement of certain organs, such as the heart wall or vessel wall. For example, the thickness of the heart wall changes over time during each heartbeat while the heart is contracting and expanding. To diagnose certain heart conditions it is necessary to track down dynamically the alteration of the heart wall thickness or of other critical organ parameters. Many clinical measurements can be realized, such as, heart thickness as a function of time at a specific heart location, which is an important application for an echocardiography. Especially with the use of ultrasound or radiology image systems, it is difficult to obtain such measurements because the objects investigated, such as a heart wall, are often part of a larger object, which can move or contract and thereby make measurements of specific areas nearly impossible.

SUMMARY OF THE INVENTION

It is therefore that objective of the present invention to provide a method of dynamically and accurately measuring the movement of objects. The method according to the present invention for dynamically measuring movement of objects using image processing provides the steps of     receiving a sequence of images,     determining at least a first and second reference point within a first image,     defining identification areas around the reference points,     searching within a sequential image a search area around the predefined reference points which best match the identification area,     determining the displacement of the reference point.

In another embodiment the present invention provides a method of dynamically measuring movement of objects using image processing with the steps of:

a) receiving a sequence of images, b) determining at least a first and second reference point within a first image, c) defining identification areas around the reference points, d) searching within a sequential image a search area around the predefined reference points which best match the identification area, e) determining the displacement of the reference point, and repeating steps c) to e) for all images whereby the points which best match the reference points are used as new reference points.

Yet another embodiment comprises an ultrasound imaging system for dynamically measuring movement of objects using image processing including means for generating a sequence of images, input means for determining at least a first and second reference point within a first image, processing means for defining identification areas around the reference points and for searching within a sequential image a search area around the predefined reference points which best match the identification area, and for determining the displacement of the reference point.

DETAILED DESCRIPTION OF THE INVENTION

Figure 1:
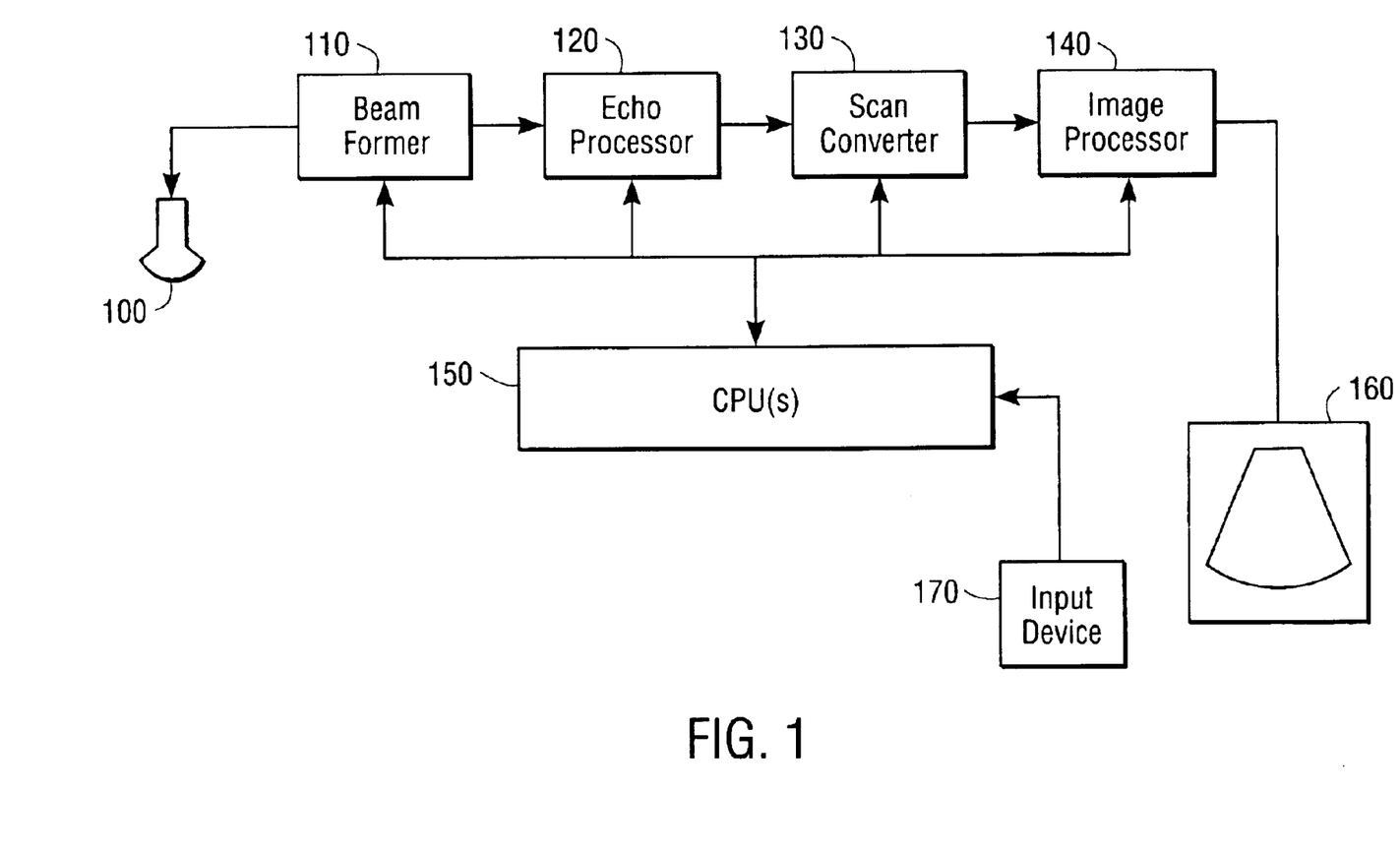
FIG. 1 shows a block diagram of an embodiment of the present invention.

FIG. 1 is a block diagram of an ultrasound system that produces sequential images of an object of interest and comprises a transducer. The ultrasonic transducer 100 comprises an array of piezoelectric crystals that deliver ultrasonic energy into a patient and receive ultrasonic echoes from the patient. Electrical signals representative of the echoes produced by the transducer 100 are delivered to a beam former 110 where they are selectively combined to produce an indication of the echo intensity along a particular direction or beam in the patient. The data produced by the beam former 110 is fed to an echo processor 120 that calculates an echo intensity at each position along a beam and may calculate a Doppler shift of the echoes received along a particular beam. Data from the echo processor 120 is fed to a scan converter 130 that converts the data into a form that can be readily displayed on a video monitor. This arrangement generates a series of images with a specified frame rate.

The data produced by the scan converter is stored in an image processor 140, for example, on a hard drive, where an additional processing, such as adding color, may be performed prior to displaying the images on a video monitor 160. The image processor may include one or more digital signal processors (DSPs) for further enhancement and/or processing. Controlling the operation of the above-referenced parts are one or more central processing units 150. The central processing units 150 also receive commands from a user through a variety of controls (not shown) that allow the user to adjust the operation of the ultrasound machine. A light pen, a mouse input-device 170 or any other input device is coupled with the central processing unit 150 to allow a user to define specific points of interest on the screen 160.

According to the present invention one parameter of an object, such as length, thickness, volume, or any other parameter shall automatically be measured. Therefore specific points of interest which define this parameter have to be input by a user. For example, the regional heart wall thickening analysis requires that both the epicardial and endocardial interfaces be identified from M-mode or brightness mode (B-mode) images. This can be done by defining reference points on the first image of an image series whose relationship to each other represent the respective parameter. For example, the instantaneous spatial difference between the signals reflected from these two surfaces represent myocardiac wall thickness, which, if tracked throughout the cardiac cycle, would provide real-time quantitative measurement of regional myocardial wall thickening. As mentioned above, unfortunately, continuous detection of both epicardial and endocardial backscatter peaks from specific part is not accurate with the M-mode imaging technique in vivo, due to organ's orientation, motion and contraction, and different signals from different heart location. These additional factors might have a significant influence on the respective parameter to be measured and therefore falsify the measurement results.

According to the present invention, for example, the internal tissue displacements for specific locations can be tracked accurately by using both a coarse-scale search with image-based tracking technique and a fine-scale search with RF or I/Q signals cross-correlation technique as will be shown in more detail below. Initially, a user inputs the points of interest which define the measured parameter through a light pen or a mouse input device 170. Once these points of interest are input, the system automatically tracks these points of interest in the following pictures and calculates the parameter change between the succeeding images, and stores the changes from image to image over time. The results can be shown in another screen displaying a graph of the parameter over time.

Figure 2:
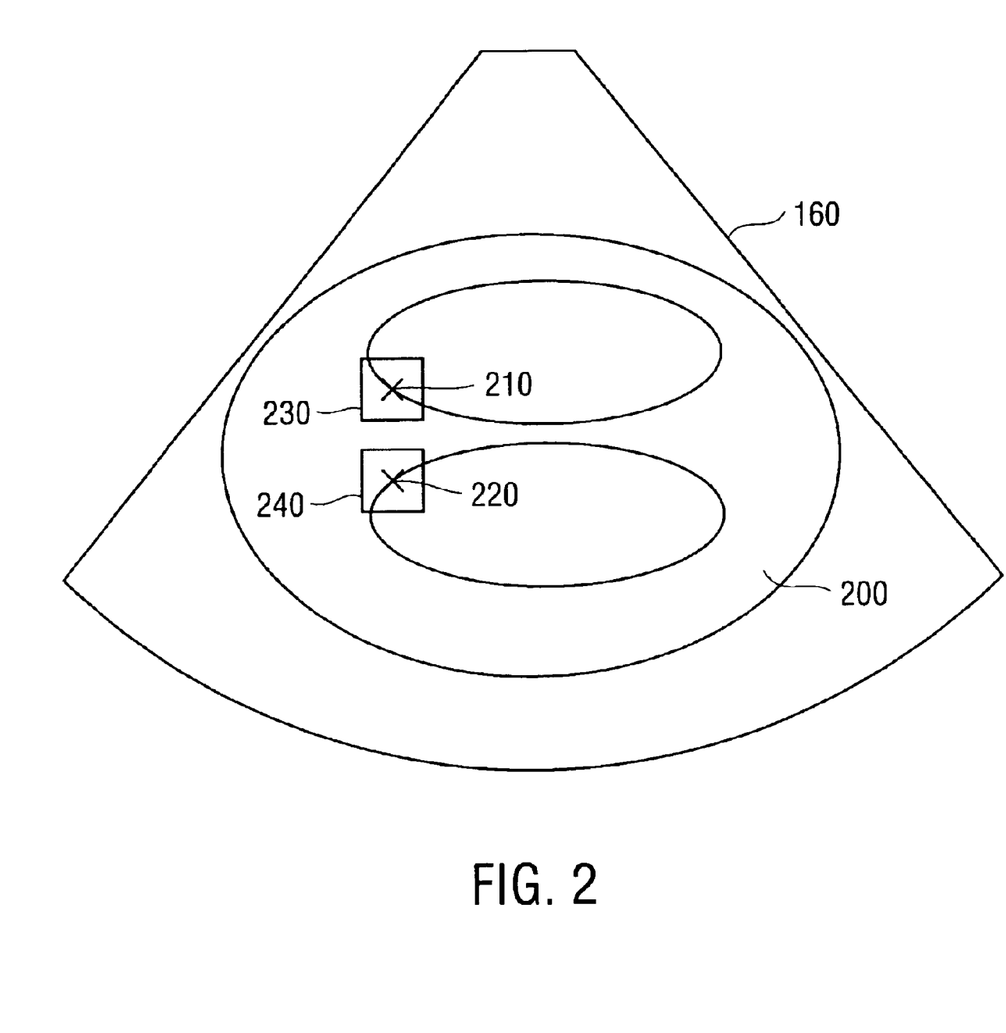
FIG. 2 shows a first image setup according to the present invention.

In order to simplify the analysis, two succeeding B-mode images and their respective RF echo fields are received from the scan converter 130 and fed to image processor 140. At first, several specific points of interest on the first image are selected manually by a user. FIG. 2 shows such a first image displayed on the screen 160 of an ultrasound machine. The screen displays, for example, an object 200. A user may define multiple points of interest by means of an input device 170. In FIG. 2 the user defined two points of interest 210 and 220. The analyzed parameter shall be the distance between these to points of interest. Centered with these selected points 210 and 220, kernels 230 and 240 are created and defined with the size of N pixel points in lateral direction and M pixel points in axial direction for the first B-mode image. Then, search regions will be defined for the succeeding image with the size of N+2δN pixel points in lateral direction and M+2δM pixel points in axial direction for the second B-Mode image. The following search will be done for each kernel at 2δN by 2δM locations. At each location, a sum-absolute-difference (SAD) value is computed, whereby each SAD kernel has M×N points. The SAD value is evaluated for each (I,j) until a minimum of SAD occurs which will be the best match of the respective kernels of the first and second image. These values also represent the new points of interest for a following image and new values are calculated in the same manner for all following images of a series. The respective equation is represented by:

$$SAD(i, j) = \sum_{n=1}^{N} \sum_{m=1}^{M} \|I_{m,n} - J_{m+i,n+j}\|$$

where I and J are the grade levels (B-mode image intensities) at the user specific locations from these two B-mode images. The parameters I and J are within the following ranges: $-\delta n <= I <= \delta n$, $-\delta m <= j <= \delta m$. The displacements in both lateral and axial directions are given by X1=id and Y1=jd, whereby d is the image pixel size. This gives the first step search or so-called coarse-scale search. For ideal cases, where noise signals are relatively small compared to the echo signals, the accuracy of this search is mainly limited by the pixel size of the B-image. For example, using a 2.5PL20 probe for cardiac imaging in vivo with a depth of 80.0 mm, the pixel size is about 0.17 mm, which is much smaller than other uncertainties caused by other artifacts, such as the variation of speed of sound or the organs complex motion.

Figures 3A, 3B:
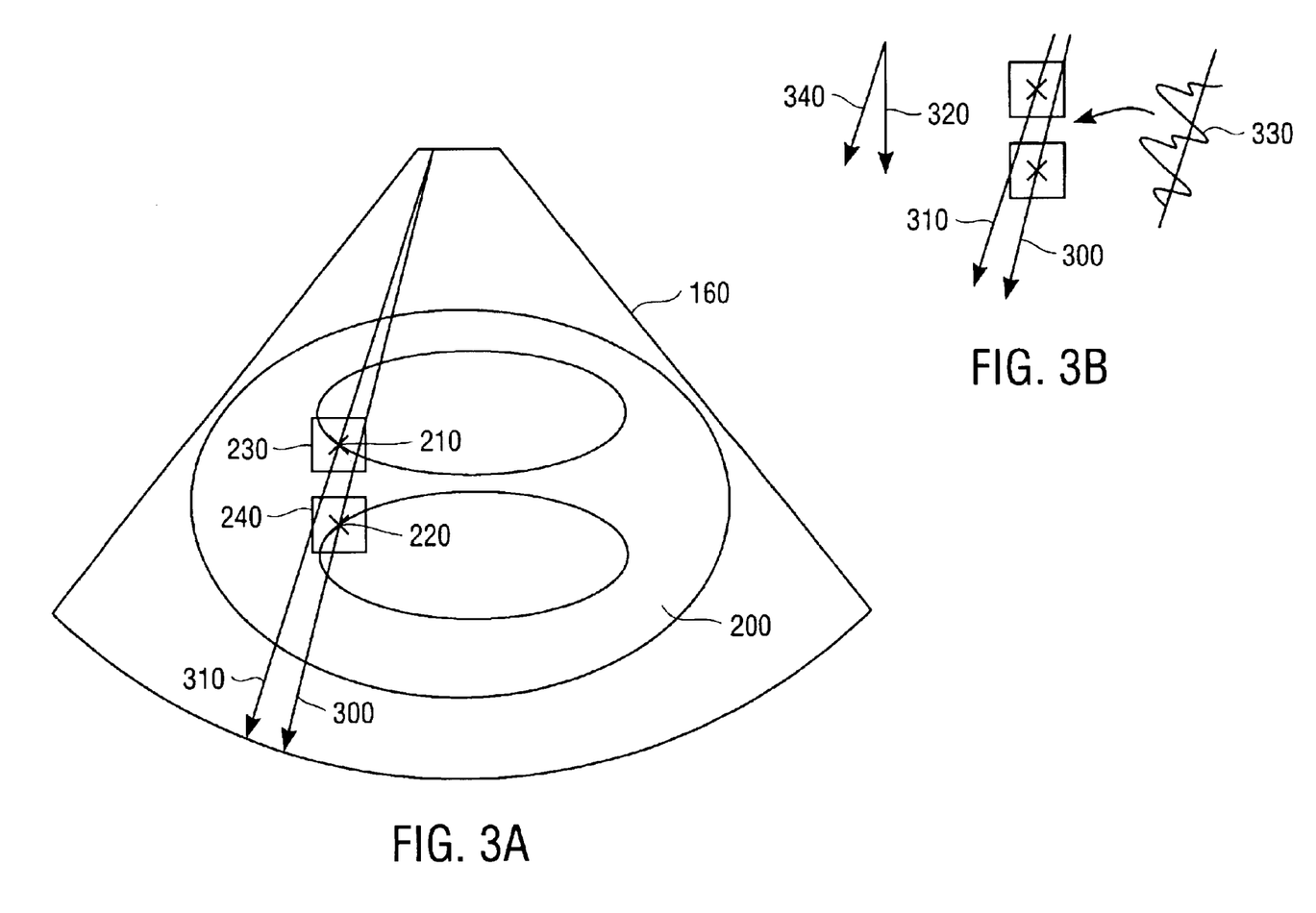
FIG. 3 shows a second image setup according to the present invention.

FIG. 3A shows the same scenario as FIG. 2, whereby two ultrasound wave lines 300 and 310, the so-called A-lines are indicated. FIG. 3B shows these A-lines in detail with additional information. Arrow 320 indicates the ultrasound depth direction and arrow 340 the respective A-line direction. Numeral 330 indicates a respective RF signal, for example, in the selected regions of interest. The lateral resolution of an ultrasound image is usually much less than the axial resolution if the RF signals are taking into account. The axial resolution is therefore only limited by the wavelength.

Therefore, in order to increase the accuracy of the displacements estimation, a second step search, the so-called fine-scale search, can be done. This fine-scale search is based on the correlation of RF or I/Q signals within the same locations. Again, these regions of interest are selected manually by a user as indicated in the first step search. This fine-search is also based on an estimate of the residual displacements in both axial and lateral directions, as shown in FIGS. 3A and 3B. In that case, a synchronization needs to be made between B-mode image data and I/Q data, in order to get the information from the same location. Then, the I/Q signals are windowed and centered at the giving locations. The fine-scale motion along A-lines 300 and 310 can be estimated from the phase of their zero-lag correlation functions:

$$t = \frac{\tan\left[\frac{\text{Im}(C(0))}{\text{Re}(C(0))}\right]}{\omega_0}$$

where C(n) is the complex based-band correlation function form the I/Q signal data, and $\omega_0$ is the ultrasound angular frequency.

A limitation associated with phase processing is that aliasing occurs if the displacement exceeds a quarter of an ultrasound wavelength (i.e., $\lambda/4$) where $\lambda$ is the ultrasound wavelength. To overcome this limitation and improve echo signals coherence, the results of coarse-scale displacement components in the direction of A-lines 300, 310 as an initial shift in that line 300 and 310 is used and the additional time shift t based on about a correlation function is determined. This is because the uncertainty for the coarse-scale search is about the range of the partial pixel size, which could be much more than the ultrasound wavelength. Finally, an additional displacement shift in the A-line 300, 310 direction can be determined by I=ct/2, where c is the speed of sound in the image fields (c=1.54 mm/μs).

As shown in FIG. 3A., the final displacements in both axial and lateral directions can be determined by the sum of both coarse and fine scale searches: X=id+Isinα and Y=jd+Icosα, where a is the angle between the direction of the A-line 340 and the direction of image depth 320. Using the same approach, all selected points' motions can be determined and their relative positions can be estimated. Similarly, the motion from the second image to the third image can be estimated, and so on. Finally, the motions (displacements) can be determined as a function of time (or the number of frame).

Figure 4:
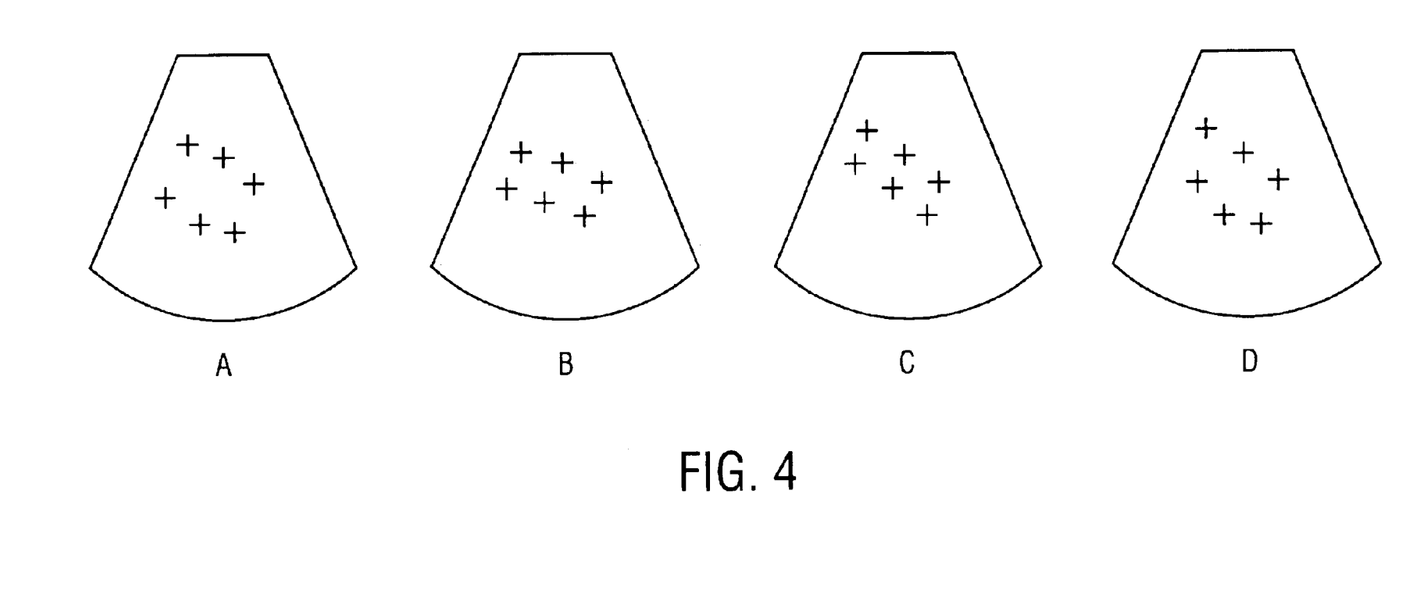
FIGS. 4A–D shows different images to be processed according to the present invention.
Figure 5:
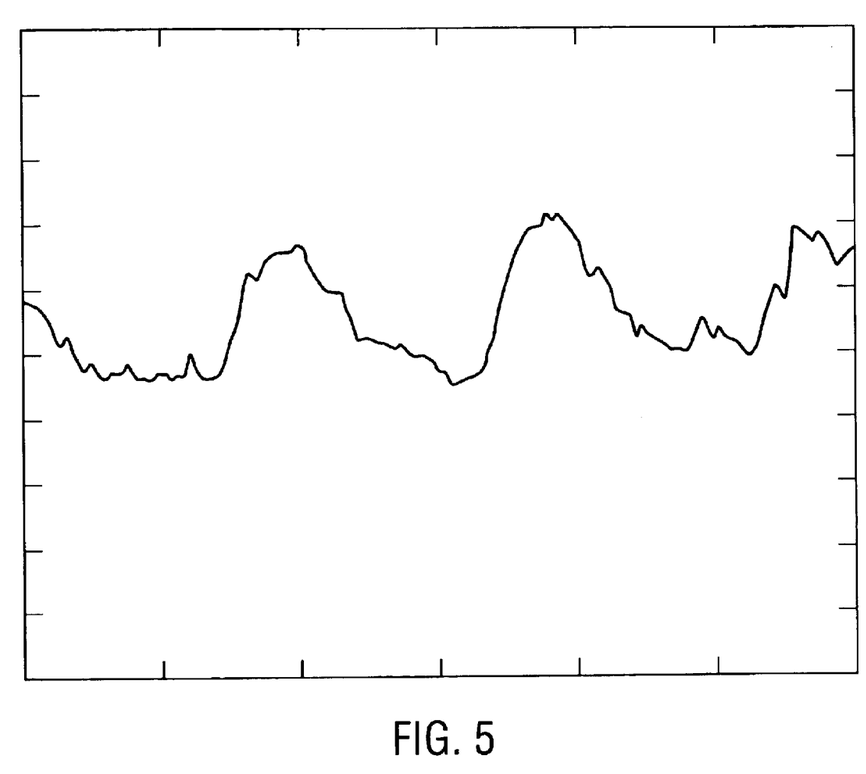
FIG. 5 shows a resulting graph achieved by the method according to the present invention.

In an example, a human heart can be scanned with a frame rate of 31 frames/ second, whereby the image depth can be set to 80 mm. FIGS. 4A–D shown example is of several B-mode images, which are used to show the heart wall thickness over time, for example over two cardiac cycles. Once these images have been reported, several interest points along each of the heart wall's on the first image as shown in FIG. 4 a, are marked. Based upon the above tracking technique, the displacements of these points will be determined as a function of time, as shown in FIGS. 4B–4D. The relative distances along these points as a function of time can then be calculated. For example, based on the two specific points on the two sides of the heart wall, the distance between these two points (called the wall thickness) can be calculated as a function of time and is shown in FIG. 5. This method eliminates most of the influencing parameters, such as organ movement, contraction, or orientation shifts.

In more general applications for this technique, the distance among selected points, such as two points beside the thickness of organ wall's, and the area covered by the selected points, such as the volume of the organ can be measured. The results can be displayed quantitatively as shown in FIG. 5. The results can also be displayed in curves like the M-mode, or in color coding on the original B-mode image in real-time, e.g. for the normal and abnormal tissue's differentiation.

Figure 6:
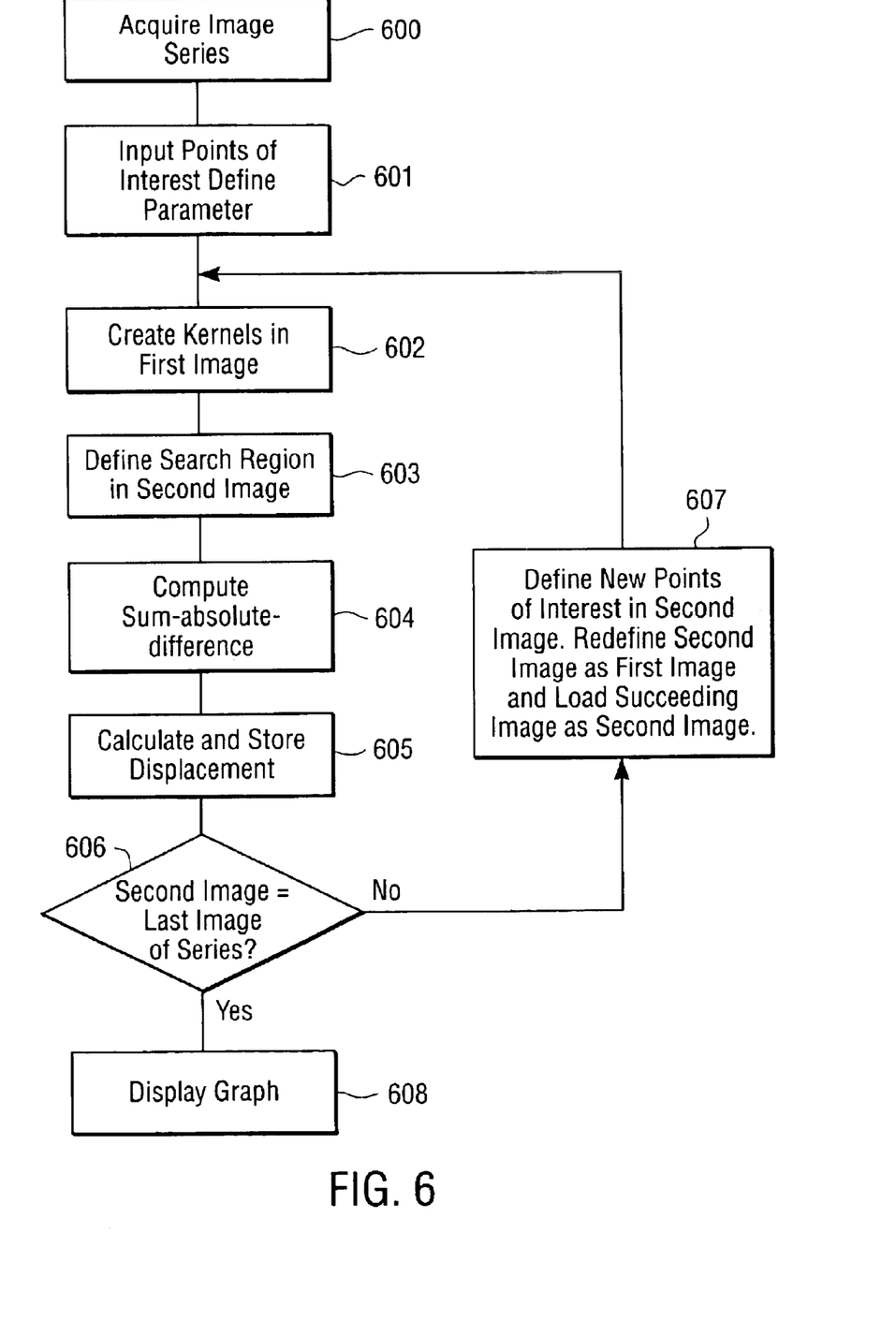
FIG. 6 shows a first flow chart of the method according to the present invention.

FIG. 6 shows a flow chart of the method according to the present invention. In a first step 600 a series of images gets acquired. These images can be generated by an ultrasound machine or any kind of device, such as X-ray devices, capable of generating sequential images. A user inputs the points of interest in step 601 and defines the respective parameter, e.g. distance, volume, etc. In step 602 the kernels are created for the points of interest in the first image. Kernels can have square shapes or circle shapes or any other appropriate shape around the respective points. The same locations of these points are used in a second or succeeding image to define the search areas. The size of the search areas depends on the respective application and on the probability of how far the points of interest can move within two image frames. In step 604 a best match calculation is performed to locate the point of interest in the second image. All these steps are done for all points of interest which define a respective parameter. Finally, in step 605, the displacement or change of the parameter is calculated and stored for later display. In step 606 it is determined whether all images of a series have been analyzed. If yes, then a graph of the analyzed parameter is displayed in step 608. If not, then the second image is re-defined as the first image in step 607 and an image which succeeds the current second image is defined as the second image. The points of interest will now be the best match points calculated in step 604. This is done for all images of a series. Of course, with every calculation of a displacement the respective parameter change can be displayed immediately instead of in the final step 608.

Figure 7:
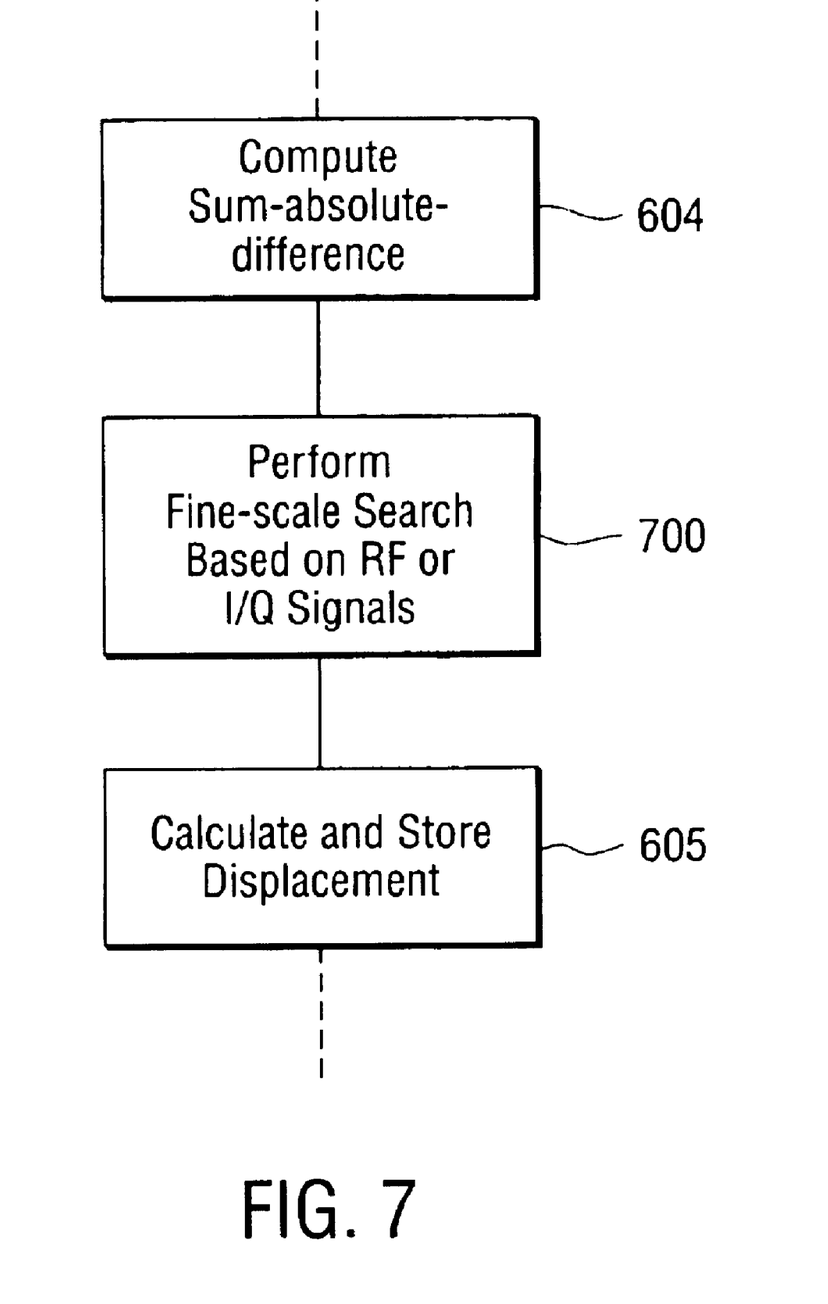
FIG. 7 shows a second flow chart of the method according to the present invention.

FIG. 7 shows an additional step inserted between steps 604 and 605 of FIG. 6. This additional step performs a fine-search based on the RF or I/Q signals as described above. This additional step can enhance the accuracy in axial direction of an ultrasound scan. If the parameter to be analyzed is an absolute value rather than a relative, then, for example, a first and second point of interest can be set identical or only a single point of interest is used. Thus, an absolute displacement value can be achieved.

The present invention can be used with any kind of ultrasound, radiology or MR system. The only condition that has to be met is that a sequence of images has to be created, for example, similar to an image sequence generated with a movie camera. Nevertheless, a real-time condition is not necessary but in many circumstances useful. The images can be stored digitally or analog. Analog pictures can be digitized at a later time to be processed most efficiently according to the present invention.

What is claimed is:

1. Method of dynamically measuring movement of objects using image processing:

receiving a sequence of images;

determining from user input at least first and second reference points within a first image;

defining identification areas around said first and second reference points;

searching within a sequential image a search area around points corresponding to said first and second reference points which best match said identification areas; and determining the displacement of said first and second reference points;

wherein said searching includes a first coarse-scale search and a fine-scale search, said fine-scale search being based upon the correlation of RF signals having a resolution greater than a resolution of the images.

2. Method according to claim 1, wherein said identification area has a square shape.

3. Method according to claim 1, wherein said identification area has a circular shape.

4. Method of dynamically measuring movement of objects using image processing:

a) receiving a sequence of images;

b) determining from user input at least first and second reference points within a first image;

c) defining identification areas around points corresponding to said first and second reference points;

d) searching within a sequential image a search area around said first and second reference points which best match said identification areas;

e) determining the displacement of said first and second reference points; and f) repeating steps c) to e) for all images whereby points corresponding to the displacement from the first and second reference points are used as new reference points;

wherein said searching includes a first coarse-scale search and a fine-scale search, said fine-scale search being based upon the correlation of RF signals having a resolution greater than a resolution of the images.

5. Method according to claim 4, wherein said identification area has a square shape.

6. Method according to claim 4, wherein said identification area has a circular shape.

7. Ultrasound imaging system for dynamically measuring movement of objects using image processing:

means for generating a sequence of images;

input means for determining from user input at least first and second reference points within a first image;

processing means for defining identification areas around said reference points and for searching within a sequential image a search area around points corresponding to said predefined reference points which best match said identification areas, and for determining the displacement of said reference points;

wherein the processing means includes searching with a coarse-scale search and a fine-scale search, said fine-scale search being based upon the correlation of RF signals having a resolution greater than a resolution of the images.

8. Method of dynamically measuring movement of objects using image processing:

receiving a sequence of images;

determining from user input at least first and second reference points within a first image;

defining identification areas around said first and second reference points;

searching within a sequential image a search area around points corresponding to said first and second reference points which best match said identification areas; and determining the displacement of said first and second reference points;

wherein said searching includes a coarse-scale search and a fine-scale search, said fine-scale search being based upon the correlation of RF or I/Q signals.

9. Method of dynamically measuring movement of objects using image processing:

receiving a sequence of images;

determining from user input at least first and second reference points within a first image;

defining identification areas around said first and second reference points;

searching within a sequential image a search area around points corresponding to first and second reference points which best match said identification areas; and determining the displacement of said first and second reference points;

wherein said searching includes a coarse-scale search and a fine-scale search, said fine-scale search being based upon the correlation of coherent signals and having a resolution greater than a resolution of the images.

* * * * *